United States Patent [19]
Shumate et al.

[11] Patent Number: 5,324,480
[45] Date of Patent: Jun. 28, 1994

[54] LIQUID HANDLING SYSTEM

[75] Inventors: Christopher B. Shumate; Eric Riedi, both of Reno; Doud R. Branham, Sparks; Harold R. Schultz, Reno, all of Nev.

[73] Assignee: Hamilton Company, Reno, Nev.

[21] Appl. No.: 986,423

[22] Filed: Dec. 4, 1992

[51] Int. Cl.[5] .................. G01N 21/00; B01L 3/02; E03B 1/00
[52] U.S. Cl. ....................... 422/63; 422/100; 73/864.01; 73/864.11; 73/864.13; 73/864.14; 137/602
[58] Field of Search ............... 422/100, 63; 73/864.01, 73/864.11, 864.13, 864.14; 137/602, 889

[56] References Cited

U.S. PATENT DOCUMENTS

| | | | |
|---|---|---|---|
| 3,632,119 | 1/1972 | Carpenter | 422/100 |
| 3,912,456 | 10/1975 | Young | 422/100 |
| 4,677,987 | 7/1987 | Choski | 128/719 |
| 4,678,752 | 7/1987 | Thorne et al. | 435/291 |
| 4,679,446 | 7/1987 | Sheehan et al. | 73/864.13 |
| 4,730,631 | 3/1988 | Schwartz | 134/155 |
| 4,980,297 | 12/1990 | Haynes et al. | 436/178 |
| 5,078,970 | 1/1992 | Teodorescue et al. | 422/100 |
| 5,079,170 | 1/1992 | Rosman et al. | 436/178 |

Primary Examiner—James C. Housel
Assistant Examiner—N. Bhat
Attorney, Agent, or Firm—Gregory Garmong

[57] ABSTRACT

A liquid handling system includes a translation mechanism, and a probe mounted on the translation mechanism. The probe has a number of lumens extending along the length of the probe. The lumens are open at their lower ends and connectable at their upper ends to a compressed air source and sources of liquid solvents. The system further includes multiple seal heads that can be attached to the lower end of the probe to perform various functions. Some seal heads seal to the tops of various sized containers placed below the probe, with a cylindrical splash guard overlying the exterior of the top of the container to prevent splashes that might injure personnel. Other seal heads rotatably attach to other structures, such as filters. The seal heads may be parked and then used, one at a time, by inserting the probe into the appropriate seal head. After use, the seal head is returned to the parking location and drawn off the end of the probe.

18 Claims, 3 Drawing Sheets

LIQUID HANDLING SYSTEM

BACKGROUND OF THE INVENTION

This invention relates to a liquid handling system used in chemical analyses, and, more particularly, to such a system suited for automated operation with multiple functions.

Modern analytical chemical techniques often utilize a series of liquid handling steps that must each be applied to a large number of samples. For example, in solid phase extraction, columns of absorbent are used to separate the components of a liquid sample, and particular components are removed for further analysis. In a typical case, the column is first conditioned with the addition of a fluid. The sample is applied, possibly after being filtered, and the column is washed with a solvent to separate the component of interest. The component of interest is then eluted with yet another solvent and transferred to further analytical apparatus.

Some analytical laboratories process hundreds of samples using solid phase extraction or other techniques. Since the steps are highly repetitive, automated systems have been developed to reduce the manual labor involved in the liquid handling and processing. Such systems are commercially available and widely used.

Existing systems have shortcomings that limit their usefulness, however. One important problem arises in the wide variety of samples studied and the absence of a single standard size for the various columns, tubes, and vessels utilized in liquid handling operations. For example, an analytical laboratory may receive samples for analysis in a number of different-sized sample containers. It may be necessary to pour the sample into a single-size container that can be handled by the automated analytical apparatus. If a range of sizes are used in the analytical apparatus, there may be safety risks from splashing and spraying of fluids into the air, particularly when pressure is applied to the sample containers or columns in certain procedures. The result of this problem is that hand operations may be required that reduce the efficiency of the otherwise-automated analytical system.

There is a need for improved automated apparatus for performing analytical procedures without the need for operator intervention and minimizing the manual tasks required before, during, or after the analytical procedure. The present invention fulfills this need, and further provides related advantages.

SUMMARY OF THE INVENTION

The present invention provides an automated liquid handling apparatus of great versatility. It may be used in a variety of liquid handling functions, such as those encountered in solid phase extraction procedures. The apparatus permits the utilization of a variety of tubes and containers, and related apparatus. It automates a greater range of the liquid handling functions, and provides a high degree of operator safety. Additionally, it is compatible with existing liquid surface sensors used to control the vertical movement of probes.

In accordance with the invention, a liquid handling system comprises a translation mechanism, and a probe mounted on the translation mechanism, the probe having a lower end and an upper end. The system further includes a first seal head having means for sealing the first seal head against an upper end of a cylindrical container having a first diameter positioned below the probe, and a first splash guard sleeve overlying the exterior of the first seal head, the first splash guard sleeve being dimensioned to fit over an exterior surface of the first cylindrical container when the first seal head is sealed against the first cylindrical container. There is further a means for removably attaching the first seal head to the lower end of the probe.

Since the seal head is removable, it may be removed from the probe and placed at a parking location. Another seal head, comparable to the first seal head in structure but sized to fit other sizes of cylindrical containers or other disposables, can be attached to the probe and used, without interfering with the operability of the probe. Other seal heads can perform other functions, such as attaching to a tapered Luer lock.

In another aspect of the invention, which is compatible with the seal head approach, a liquid handling system comprises a translation mechanism, and a probe mounted on the translation mechanism, the probe having a lower end and an upper end. The probe comprises a plurality of lumens extending along the length of the probe, the lumens being open at their lower ends and including means for connecting to an external source at their upper ends. The system includes sources of consumables typically used in the analytical procedures, such as compressed air and various solvents. These are piped to the various lumens, and may thence be directed into containers according to the requirements of an analytical procedure.

The present invention thus provides to the analytical laboratory the capability to work with a variety of different containers, and to supply consumables to the analytical procedures without intermixing. The system includes convenience and safety features. Other features and advantages of the invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
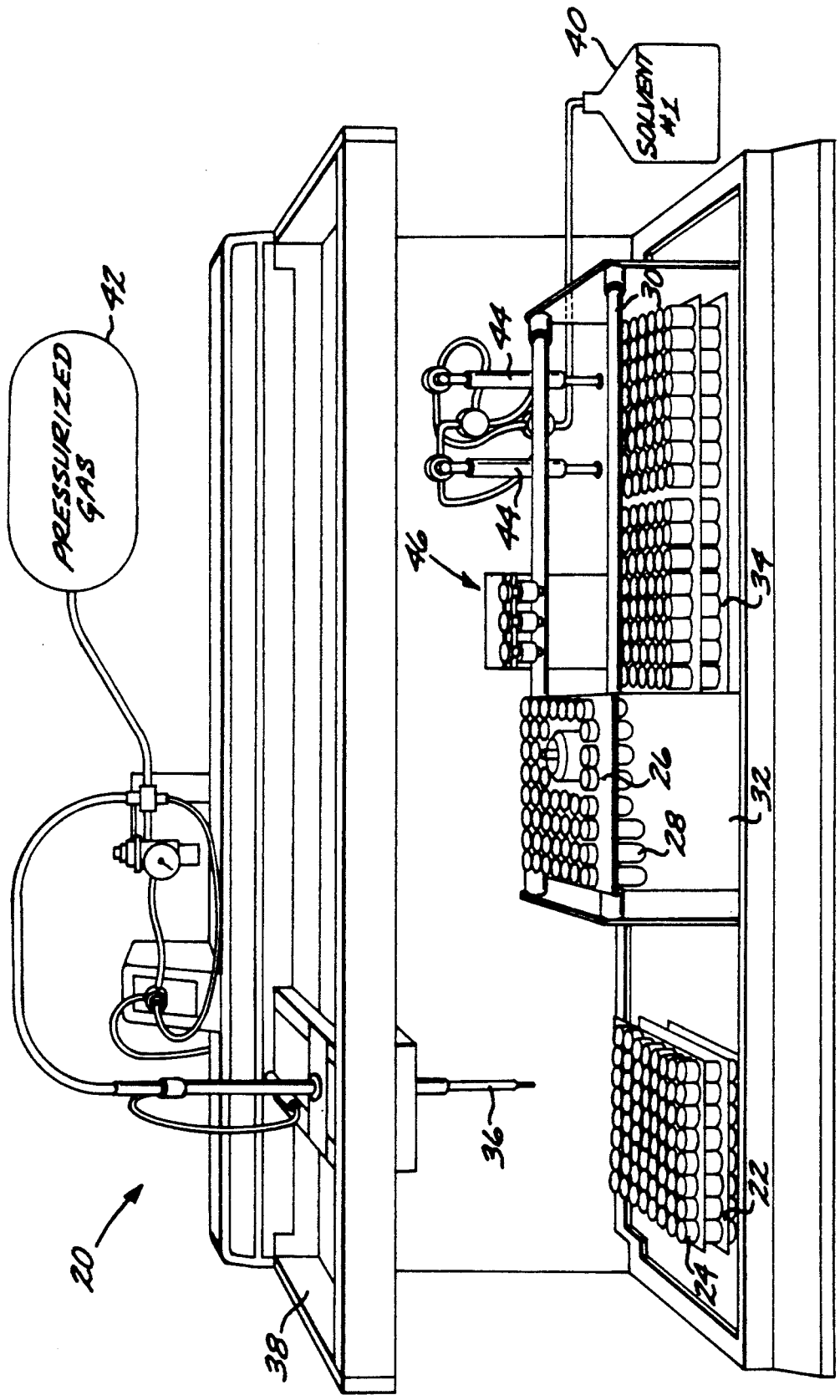
FIG. 1 is a perspective view of a liquid handling system.

FIG. 1 depicts a liquid handling system 20, in this case specifically tailored for a preferred solid phase extraction (SPE) procedure, but not limited to such application. The system 20 includes a sample rack template 22 with space for a plurality of sample containers 24. A column carrier rack 26 receives a plurality of SPE columns 28. The column carrier rack 26 is mounted on a column switching platform 30, which permits the columns 28 to be moved horizontally between a waste collection tray 32 and a set of fraction collection containers 34. The sample containers 24, SPE columns 20, and fraction collection containers 34 are all supported in templates so that the precise location of the containers 24 and 34 and column 20 are established.

The liquid handling system permits a wide range of liquid handling operations. To transfer liquids, add liquids, and pressurize the SPE columns 20, a probe 36 is mounted on an x-y-z translator mechanism 38 above the structure described in the prior paragraph. The probe 36 may be translated in the x and y dimensions above the structure, and the probe 36 may be raised and lowered in the z dimension. Liquids such as solvents and gas pressure are supplied to the probe from liquid sources 40 and a pressurized gas source 42. Liquid is driven into the probe 36 through syringes 44 that precisely meter the amounts of liquids.

Figure 2:
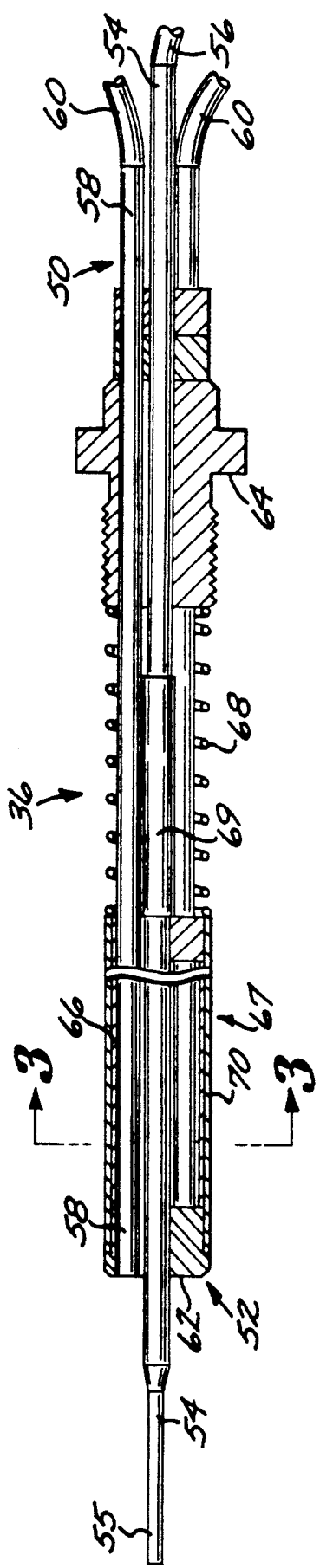
FIG. 2 is a side sectional view of a probe used in the liquid handling system of FIG. 1, taken generally along lines 2—2.
Figure 3:
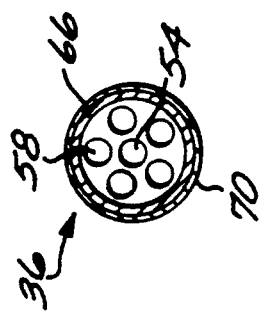
FIG. 3 is a cross sectional view of the probe of FIG. 2, taken along lines 3—3.

FIGS. 2 and 3 illustrate the probe 36 in greater detail, in sectional views. The probe is generally cylindrical, and has an upper end 50 and a lower end 52. A central lumen 54 extends down the central axis of the probe 36, and is attached at its upper end by tubing 56 to one of the syringes 44. The central lumen 54 acts in the manner of a needle to precisely dispense fluids. To this end, it has a small diameter orifice 55 that dispenses small droplets. Dispensing of a large number of small droplets rather than a small number of large droplets results in improved accuracy of dispensing. The length of the central lumen 54 and its orifice 55 are sufficiently great that it extends through the entire length of the seal head, to be described subsequently, that is attached to the lower end of the probe 36. The small diameter of the orifice region 55 also permits access to small-diameter containers and minimizes crosscontamination that results when the central lumen 54 is dipped into fluids before and during transfers.

A plurality of peripheral lumens 58, in the form of elongated tubes, extend parallel to the central lumen 54 around its periphery. In the illustrated case, FIG. 3, there are five peripheral lumens 58. One of the peripheral lumens 58 communicates at its upper end with the pressurized gas source 42. The other peripheral lumens 58 communicate through tubing 60 that extends to respective liquid sources 40, either through a pump or through one of the syringes 44. Alternatively, some of the peripheral lumens 58 may be in communication with sources of other pressurized gases.

The central lumen 54 and the peripheral lumens 58 are held in this arrangement by spacers 62 at the upper end 50 and the lower end 52. A sleeve 66 overlies the peripheral lumens 58. The sleeve 66, spacers 62, central lumen 54, and peripheral lumens 58 are joined into a single integral unit 67 with an epoxy adhesive. This integral unit 67 slides within the bore of a generally cylindrical fitting 64. The fitting 64 attaches to the x-y-z translator mechanism 38. The integral unit 67 can thereby be translated in the x-y plane, and can also translate upwardly and downwardly (the z direction) by a drive motor (not shown).

The sleeve 66 is biased downwardly (toward the lower end 52) by a spring 68 that is captured between, and reacts against, an upper end of the sleeve 66 and a lower end of the fitting 64. A sleeve travel limiter 69 in the form of a projection may be provided to limit the upward travel of the sleeve 66 against the biasing force of the spring 68. The upper spacer 62 limits the downward movement of the sleeve 66 and the integral unit 67.

The sleeve 66 is generally a hollow cylinder of small external diameter. A short distance from the lower end of the sleeve 66 a probe external recess 70 is formed in the outer periphery of the sleeve 66. The probe external recess 70 is a length of reduced diameter, used to removable join implements to the probe 36 in a manner to be discussed subsequently.

Figure 4:
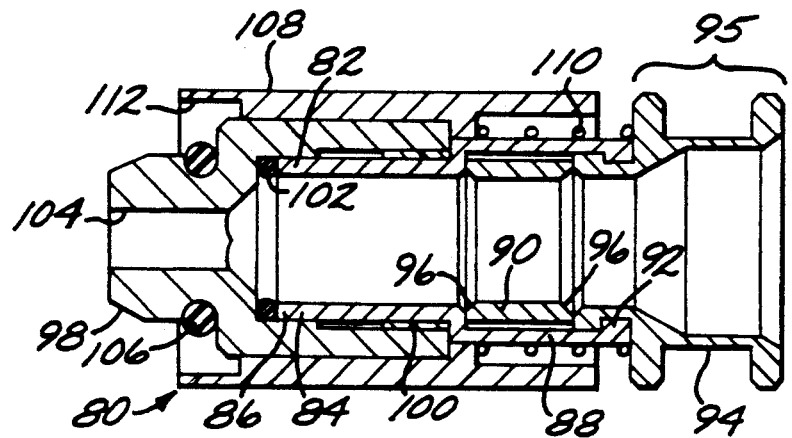
FIG. 4 is a side sectional view of a seal head removably attachable to the probe.
Figure 5:
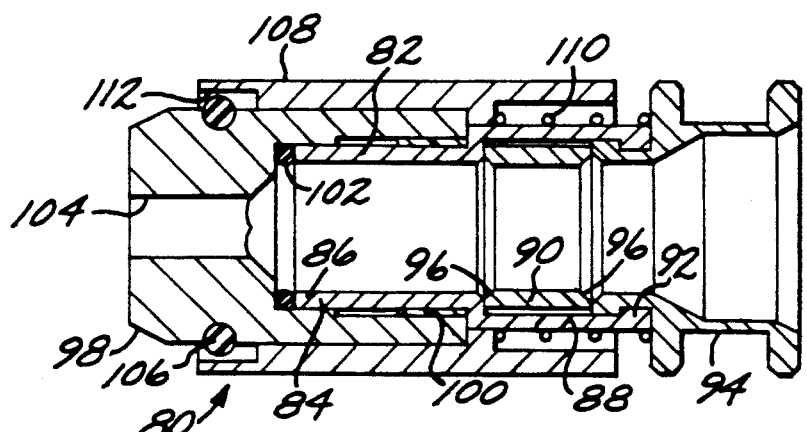
FIG. 5 is a side sectional view of another seal head removably attachable to the probe.

FIGS. 4 and 5 depict two implements that may be slidably attached to the probe 36 in a detachable and removable manner. The implements of FIGS. 4 and 5 are seal heads 80 that seal to containers or columns of varying sizes. The seal heads 80 of FIGS. 4 and 5 are identical, except as will be described in regard to the sealing structure.

The seal head 80 includes a seal head body 82, which is generally of the form of a hollow cylindrical portion 84 having a lower end 86 of one cylindrical diameter and an upper end 88 of a larger cylindrical diameter. A split-ring seal head spring 90 is received in the upper end 88. An internally extending projection 92 in the upper end 88 forms a notch for engagement of a cylindrically symmetric seal head spring retainer 94. The seal head spring retainer 94 holds the split-ring seal head spring 90 in place. The cylindrical portion 84 is dimensioned to slide over the outer surface of the probe sleeve 66. The upper end of the spring retainer 94 has a spool-like configuration 95, with a central portion and enlarged flanges on either end. The enlarged internal diameter of the retainer 94 aids in guiding the probe 36 to an engagement with the seal head 80 when the probe 36 is inserted into the seal head body 82.

As the seal head 80 is slidably engaged to the probe 36, the probe sleeve 66 slides into the cylindrical portion 84. At the point of full insertion, the split-ring seal head spring 90, which had been extended outwardly during insertion, springs inwardly to lock to the probe external recess 70. When the seal head 80 is to be removed from the probe 36, the split-ring seal head spring 90 disengages from the probe external recess 70, because bevelled edges 96 on the interior surface of the split-ring seal head spring 90 can ride over the edges of the probe external recess 70. This design has been shown to provide a reliable, secure attachment and readily accomplished detachment of the seal head 80 to the probe 36. The attachment is achieved by driving the probe 36 downwardly into the engagement while holding the seal head 80 stationary. The detachment is achieved by holding the seal head 80 stationary and drawing the probe 36 upwardly. The attachment and detachment are accomplished with a relatively small force that does not damage the system 20, the probe 36, or the seal head 80.

A head seal 98 is joined to the exterior of the seal head body 82 with a commercial thread-locking compound such as Loctite Type 222, at location 100. This thread-locking compound has a relatively weak formulation that prevents accidental unscrewing of the parts during use, but can be overcome to disassemble the seal head during inspection and maintenance. An O-ring seal 102 prevents leakage from the interior of the seal head body 82 through the joint with the head seal 98. The head seal 98 extends downwardly and has hexagonal bore 104 therethrough. The bore 104 is made hexagonal so that a standard Allen wrench can be inserted therein and used to disassemble the parts when necessary. An important advantage of the described construction of seal head is that it can be completely disassembled for cleaning and repair.

When the seal head 80 is engaged to the probe 36, the central lumen 54 extends through the bore 104. The diameter of the bore 104 is substantially larger than the outer diameter of the central lumen 54, so that there is an annular space between the central lumen 54 and the bore 104. Liquids injected through the peripheral lumens 58 flows into the interior of the seal body 82, through the bore 104, and into any container below the probe 36.

The head seal 98 is sealed to an interior surface at the top end of a container or, equivalently, a column (not shown) with an container seal O-ring 106 located in a groove on the external periphery of the head seal 98. To accommodate containers of various cylindrical diameters, the external diameter of the head seal 98 may be made larger or smaller as needed, so that larger or smaller container seal O-rings 106 are used. The only difference between the seal heads 80 of FIGS. 4 and 5 is that the head seals 98 are of different external diameters, requiring a smaller O-ring 106 in the embodiment of FIG. 4 and a larger O-ring 106 in the embodiment of FIG. 5. The external diameters of the head seals and the respective O-rings are chosen to engage the inside lip of the top of the container to optimize the character of the seal. The available sealing force is exerted through a small area, thus increasing the sealing pressure between the O-ring and the edge of the container.

When the head seal 98 is sealed to a container, the probe 36 is driven downwardly so that the O-ring 106 contacts the container. Variations in length of a particular size container are accommodated by the sliding movement of the probe sleeve 66, to which the seal head 80 is attached by the split-ring seal head spring 90. Thus, the downward sealing force of the head seal 98 to the containers is resilient in nature, preventing any damage to the containers or to the liquid handling system.

As discussed, an important function of the head seal 98 and its container seal O-ring 106 is to seal the probe 36 to a container with a pressure-tight seal. The interior of the container is pressurized through the central lumen 54 in some liquid handling procedures. There is a safety concern that liquid could splash during the pressurization from the interior of the container in the event that the seal of the O-ring 106 to the container is imperfect; or at the end of the pressurization procedure, if the seal is broken before the pressure in the interior of the container has returned to atmospheric pressure. Such splashing could cross contaminate other containers or cause injury to persons who might be working near the liquid handling system 20.

To prevent cross contamination or injury to persons, a splash guard 108 is provided over the lower end of the seal head 80. The splash guard 108 is a generally cylindrical sleeve that slidably fits over the exterior surface of the head seal 98 and the seal head body 82. The splash guard 108 is biased toward the container seal O-ring 106 by a spring 110 that is captured between an inward projection of the splash guard 108 and an outward projection on the retainer 94. The splash guard 108 has a lip 112 that projects axially downwardly to radially overlie the container seal O-ring 106, when the O-ring 106 is sealed to the upper end of a container. If liquid were to leak or splash around the O-ring 106 seal to the container, the liquid could not jet outwardly, but would instead strike the interior of the lip 112 and dribble down the side of the container. While such a loss of liquid is undesirable and seldom happens, the splash guard prevents the more serious consequences of such a leakage.

Figure 6:
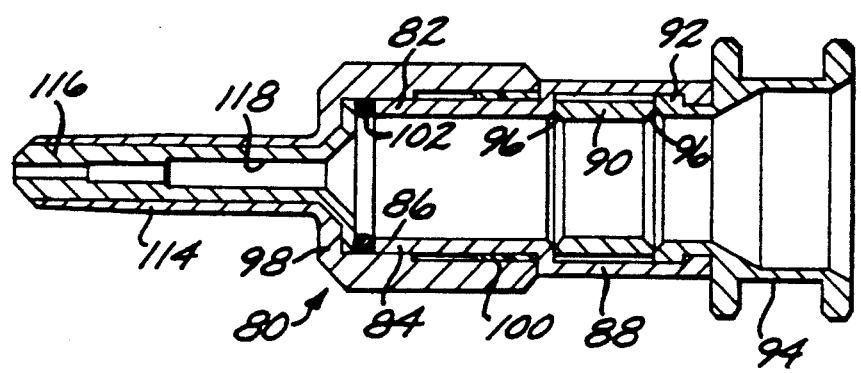
FIG. 6 is a side sectional view of another seal head used to engage a structure with a tapered interlock.

FIG. 6 illustrates another embodiment of the seal head 80. The upper end (rightmost in the view of FIG. 6) is generally of the same construction as the seal heads of FIGS. 4 and 5. The splash guard 108 and spring 110 are omitted, however. At the lower end (leftmost in the view of FIG. 6), a tapered adapter 114 forms an axial extension of the head seal 98. The exterior surface of the tapered adapter 114 is tapered inwardly from the head seal 98 to the free end. The taper is preferably selected to conform to a standard tapered Luer lock. Since the taper of the tapered adapter 114 seals to any device having a conforming tapered region, the O-ring 106 and splash guard 108 of the embodiments of FIGS. 4 and 5 are not required in the embodiment of FIG. 6.

Within the interior of the tapered adapter 114 is a tapered adapter seal 116 having an interior bore 116. The bore 116 functions in a manner similar to the bore 104, by permitting the central lumen 54 to reach the region below the seal head 80.

The seal head 80 of FIG. 6 is removably attachable to any device having a conformable tapered interlock. The seal head 80 is forced downwardly into frictional engagement with the stationary device to achieve the attachment, and is pulled up from the stationary device to disconnect.

Figure 7:
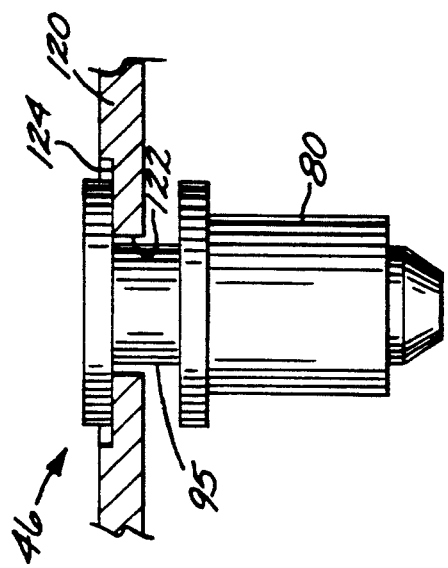
FIG. 7 is a side sectional view of the seal head parking station, with a seal head in place.

The liquid handling system 20 permits the use of a range of implements such as those shown in FIGS. 4–6. These implements can be attached to the probe 36, used for their intended purposes, and then detached and stored for later use. To facilitate the detachment and storage, a parking station 46 is provided in the liquid handling system 20, see FIGS. 1 and 7. The parking station 46 is formed of a plate 120 having one or more slots 122 therein. Each slot 122 is of sufficient width to receive the spoollike region 95 of the retainer 94 of the seal heads 80. There is a slight recess 124 on the top side of the plate 120 adjacent the slot 122. The upper flange of the spoollike region 95 rests within the recess 124 when the seal head 80 is placed into the parking station 46. The recess 124 ensures that the seal head 80 will not shift in position due to vibrations and the like.

To pick up a seal head 80 or other implement in the parking station 46, the probe 36 is moved into position over the seal head 80 by the x-y portion of the x-y-z translator. The z portion of the translator lowers the probe 36 into engagement with the seal head 80, and achieves locking engagement by the mechanism discussed previously. The x-y portion of the x-y-z translator moves the seal head 80 sideways to clear it from the parking station 46. The seal head is replaced onto the parking station 46 by reversing these steps. The probe 36 is withdrawn by the upward z-movement of the translator 38, against the force exerted by the split-ring seal head spring 90. For the reasons previously discussed, this force is readily overcome and the separation/disengagement is complete.

The present approach gives the liquid handling system great versatility in performing a wide variety of procedures. Liquids are drawn into the probe, transferred, and other liquids are added. Containers may be safely pressurized. A wide range of standardized containers and columns may be used, due to the versatility of the seal head design and the use of the parking station. Auxiliary implements such as filters may also be engaged to the probe and utilized.

Although a particular embodiment of the invention has been described in detail for purposes of illustration, various modifications may be made without departing from the spirit and scope of the invention. Accordingly, the invention is not to be limited except as by the appended claims.

What is claimed is:

1. A liquid handling system, comprising:
   a translation mechanism; and
   a fluid transfer probe mounted on the translation mechanism providing movement to said probe the probe having a lower end and an upper end, and comprising
   a plurality of lumens extending along the length of the probe, the lumens being open at their lower ends and each including means for connecting to an external source at their upper ends, and
   probe attachment means at the lower end of the probe for removably attaching a seal head of different sizes to the lower end of the probe by operation of the translation mechanism.

2. The liquid handling system of claim 1, wherein the plurality of lumens includes six lumens.

3. The liquid handling system of claim 1, further including
   a source of compressed air, and
   means for connecting the source of compressed air to one of the lumens of the probe.

4. The liquid handling system of claim 1, further including
   a source of a liquid solvent, and
   means for connecting the source of liquid solvent to one of the lumens of the probe.

5. The liquid handling system of claim 1, wherein the liquid handling system is adapted for communicating with a first cylindrical container having a first diameter and positioned below the probe, the liquid handling system further including
   a first seal head having means for sealing the first seal head against an upper end of the first cylindrical container; and
   first seal head attachment means on the first seal head for removably attaching the first seal head to the lower end of the probe by cooperative engagement with the probe attachment means.

6. The liquid handling system of claim 5, wherein the liquid handling system is additionally adapted for communicating with a second cylindrical container having a second diameter and positioned below the probe, the liquid handling system further including
   a second seal head having means for sealing the second seal head against an upper end of the second cylindrical container; and
   second seal head attachment means on the second seal head for removably attaching the second seal head to the lower end of the probe by cooperative engagement with the probe attachment means.

7. The liquid handling system of claim 5, wherein the liquid handling system is additionally adapted for communicating with an article having a rotational engagement and positioned below the probe, the liquid handling system further including
   a third seal head having means for rotatably engaging the article having a rotational engagement; and
   third seal head attachment means on the third seal head for removably attaching the third seal head to the lower end of the probe by cooperative engagement with the probe attachment means.

8. The liquid handling system of claim 5, wherein the probe attachment means includes
   a probe external recess on an outer periphery of the probe surface, and the seal head attachment means includes
   a central bore on the seal head,
   a seal head recess on the central bore of the seal head, and
   a split ring seal head sleeve retained in the seal head recess, the split ring seal being dimensioned to engage the probe external recess when the seal head is pushed onto the probe to hold the seal head in place on the probe, and to release from the probe external recess when the seal head is drawn away from the probe.

9. The liquid handling system of claim 8, wherein the probe external recess is formed in a probe sleeve that slidably overlies the probe lumens, the probe sleeve being biased in a downwardly direction by a spring overlying the probe lumens and reactive against the probe lumens.

10. A liquid handling system adapted for communicating with a first cylindrical container having a first diameter and positioned below the probe, comprising:
    a translation mechanism; and
    a fluid transfer probe mounted on the translation mechanism providing movement to said probe the probe having a lower end and an upper end, the probe further including probe attachment means at the lower end of the probe for removably attaching a seal head to the lower end of the probe by operation of the translation mechanism;
    a first seal head comprising
    means for sealing the first seal head against an upper end of the first cylindrical container, and
    first seal head attachment means on the first seal head for removably attaching the first seal head to the lower end of the probe by cooperative engagement with the probe attachment means;
    a first splash guard sleeve overlying the exterior of the first seal head, the first splash guard sleeve being dimensioned to fit over an exterior surface of the first cylindrical container when the first seal head is sealed against the first cylindrical container.

11. The liquid handling system of claim 10, wherein the liquid handling system is additionally adapted for communicating with a second cylindrical container having a second diameter and positioned below the probe, the liquid handling system further including
    a second seal head comprising
    means for sealing the second seal head against an upper end of the second cylindrical container, and
    second seal head attachment means on the second seal head for removably attaching the second seal head to the lower end of the probe by cooperative engagement with the probe attachment means; and
    a second splash guard sleeve overlying the exterior of the second seal head, the second splash guard sleeve being dimensioned to fit over an exterior surface of the second cylindrical container when the second seal head is sealed against the second cylindrical container.

12. The liquid handling system of claim 10, wherein the liquid handling system is additionally adapted for communicating with an article having a rotational engagement and positioned below the probe, the liquid handling system further including a third seal head having means for rotatably engaging the article having a rotational engagement; and means for removably attaching the third seal head to the lower end of the probe.

13. The liquid handling system of claim 10, wherein the probe attachment means includes a probe external recess on an outer periphery of the probe surface, and the seal head attachment means includes a central bore on the seal head, a seal head recess on the central bore of the seal head, and a split ring seal head sleeve retained in the seal head recess, the split ring seal being dimensioned to engage the probe external recess when the seal head is pushed onto the probe to hold the seal head in place on the probe, and to release from the probe external recess when the seal head is drawn away from the probe.

14. The liquid handling system of claim 13, wherein the probe external recess is formed in a probe sleeve that slidably overlies the probe lumens, the probe sleeve being biased in a downwardly direction by a spring overlying the probe lumens and reactive against the probe lumens.

15. The liquid handling system of claim 10, wherein the probe comprises a plurality of lumens extending along the length of the probe, the lumens being open at their lower ends and including means for connecting to an external source at their upper ends.

16. The liquid handling system of claim 15, further including a source of compressed air, and means for connecting the source of compressed air to one of the lumens of the probe.

17. The liquid handling system of claim 15, further including a source of a liquid solvent, and means for connecting the source of liquid solvent to one of the lumens of the probe.

18. The liquid handling system of claim 10, wherein the means for sealing is an O-ring.

* * * * *